US010126265B2

United States Patent
Liu et al.

(10) Patent No.: US 10,126,265 B2
(45) Date of Patent: Nov. 13, 2018

(54) PERTURBATION ION MOBILITY MASS SPECTROMETRY AND THE METHOD OF MEASURING ION MOBILITY OF SELECTED IONS

(71) Applicant: Washington State University, Pullman, WA (US)

(72) Inventors: Wenjie Liu, Xinjiang (CN); Herbert H. Hill, Jr., Pullman, WA (US); William F. Siems, Spokane, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 77 days.

(21) Appl. No.: 15/447,179

(22) Filed: Mar. 2, 2017

(65) Prior Publication Data

US 2017/0254778 A1 Sep. 7, 2017

Related U.S. Application Data

(60) Provisional application No. 62/302,250, filed on Mar. 2, 2016.

(51) Int. Cl.
*H01J 49/26* (2006.01)
*G01N 27/62* (2006.01)
*H01J 49/00* (2006.01)
*H01J 49/06* (2006.01)

(52) U.S. Cl.
CPC ........ *G01N 27/622* (2013.01); *H01J 49/0031* (2013.01); *H01J 49/0036* (2013.01); *H01J 49/061* (2013.01)

(58) Field of Classification Search
CPC .............. G01N 27/622; H01J 49/0031; H01J 49/0036; H01J 49/061
USPC ................................ 250/281, 282, 283, 290
See application file for complete search history.

(56) References Cited

U.S. PATENT DOCUMENTS

| 9,324,550 B1 * | 4/2016 | Jones ................... G01N 27/622 |
| 2004/0094709 A1 * | 5/2004 | Bateman ............... H01J 49/004 250/292 |
| 2005/0199799 A1 * | 9/2005 | Takada ................ H01J 49/0095 250/288 |
| 2011/0133076 A1 * | 6/2011 | Miller .................. G01N 27/624 250/287 |
| 2015/0276676 A1 * | 10/2015 | Jiang .................... G01N 27/622 250/282 |

* cited by examiner

*Primary Examiner* — Nicole Ippolito
(74) *Attorney, Agent, or Firm* — Whitham & Cook, P.C.

(57) ABSTRACT

The methods herein provide for analysis of ion populations. Certain aspects include: directing a continuous gas phase ion beam into an entrance of a drift tube configured within an ion mobility spectrometer; perturbing the flow of the continuous gas phase ion beam within a perturbation time range so as to cause one or more configured perturbations; configuring the drift tube to allow the one or more perturbations to separate due to the differences in mobilities; receiving the plurality of ions and the one or more perturbations at the entrance of a mass spectrometer; recording raw data indicative of the plurality of ions; and reconstructing the raw data to obtain one or more mass to charge and one or more ion mobility spectrum of the plurality of ions.

18 Claims, 8 Drawing Sheets

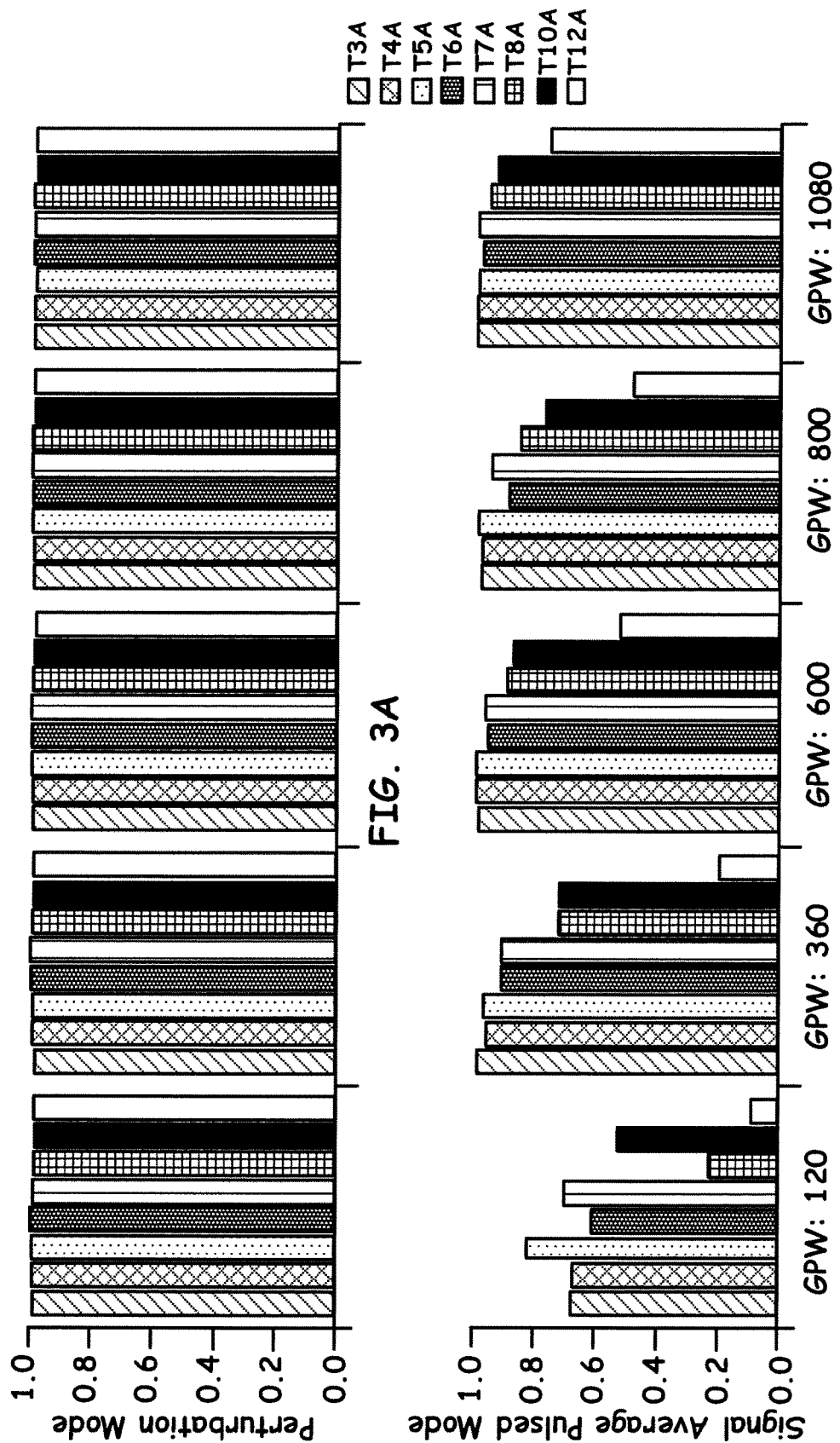

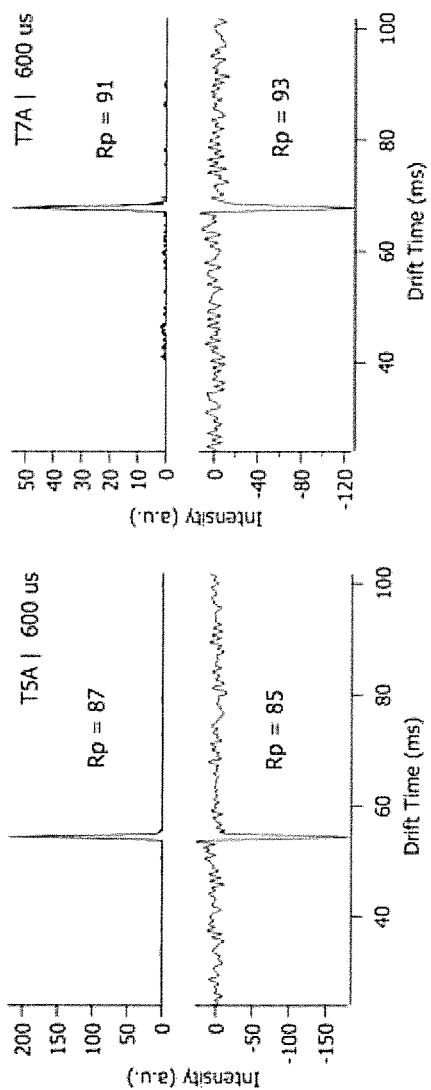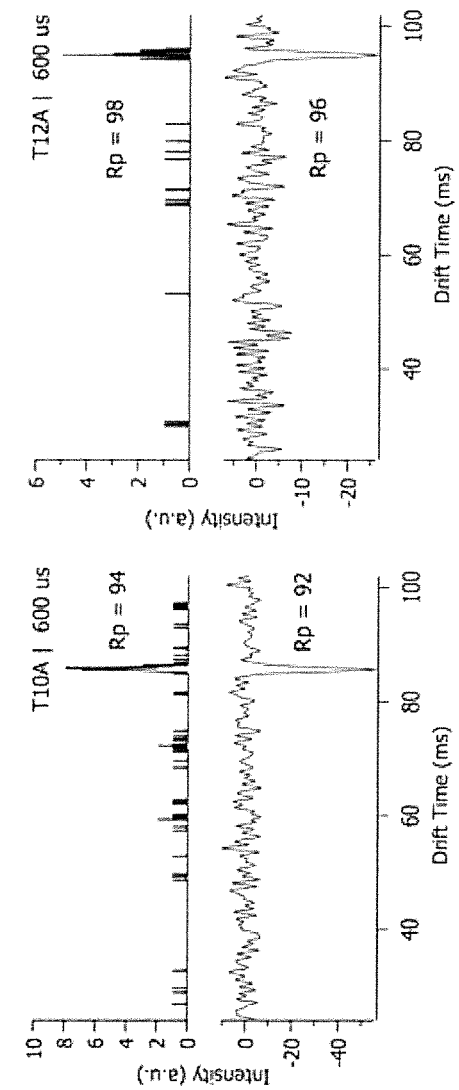
FIG. 5A  FIG. 5B  FIG. 5C  FIG. 5D

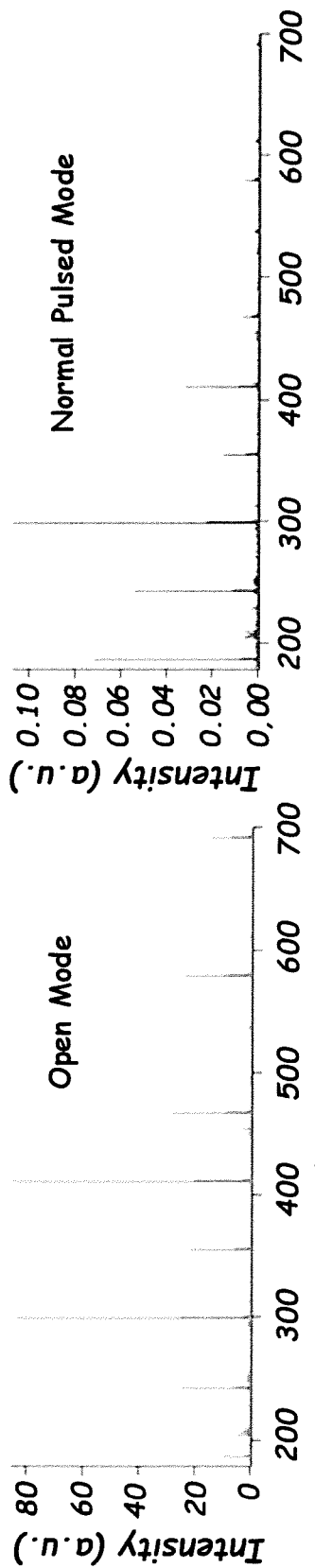
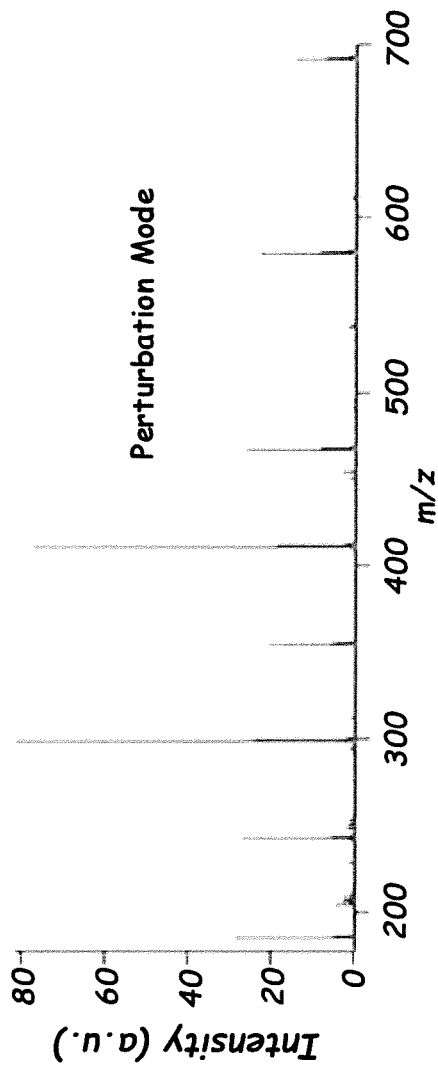
FIG. 6A  FIG. 6B  FIG. 6C

PERTURBATION ION MOBILITY MASS SPECTROMETRY AND THE METHOD OF MEASURING ION MOBILITY OF SELECTED IONS

CROSS-REFERENCE TO RELATED APPLICATION(S)

The present application claims under 35 U.S.C. § 119, the priority benefit of U.S. Provisional Application No. 62/302,250 filed Mar. 2, 2016. The disclosure of the foregoing application is incorporated herein by reference in its entirety.

BACKGROUND OF THE INVENTION

Field of the Invention

The present invention relates to the field of Ion Mobility Mass Spectroscopy (IMMS). More particularly, the present invention relates to a Perturbation Ion Mobility Mass Spectrometry (PIMMS) methodology and system to enhance, for example, ion efficiency and thus sensitivity using such instrumentation.

Discussion of the Related Art

The utility of ion mobility spectrometry (IMS) for separation of ions has been demonstrated extensively, but IMS combined with mass spectrometry (MS) has remained a niche technique, mainly because of the loss of sensitivity due to ion losses within the combination of techniques. IMS, in particular, remains a needed and desired technique to be coupled with MS because of the speed of the separation technique. Specifically, IMS exploits the beneficial aspect that different particles diffuse through a gas at different speeds, depending on their collision cross-sections with the introduced gas molecules. While neutrals diffuse randomly (via Brownian motion), ions in an applied electric field drift in a defined direction with the velocity controlled by their mobility (K). Such a quantity generally varies with the field intensity E but IMS is often run in a low-field regime where K (E) is substantially constant. In that limit, K depends on the ion/buffer gas collision cross-section 106, which allows a spatial separation of different ions.

The IMS concept of measuring size-to-charge ratio is also beneficially complementary to the principle of measurement in mass spectrometry (MS) of mass-to-charge ratio (m/z). When combined with MS, ion mobility-mass spectrometry (IMMS) represents a powerful analytical combination capable of distinguishing ions based upon both size and mass-to-charge ratios. A particular beneficial IMS analytical tool is a drift-tube ion mobility spectrometer (DT-IMS) based on the ability to rapidly screen passengers, cargo, and the surrounding environment for narcotics, explosives, and chemical warfare agents. DT-IMS also finds utility as an informative tool to probe gas-phase ion chemistry, kinetics, and under select conditions gas-phase ion conformations. DT-IMS refers to all ion mobility separation devices that cause ions to arrive at a detector at different times based on their ion mobilities; these devices sometimes are called by different names or abbreviations, e.g. traveling wave ion mobility separation device. As with many time-dispersive techniques however, challenges related to duty cycle are quite common when utilizing DT-IMS instruments. The duty cycle in most DT-IMS experiments is usually on the order of <1% and this limitation in ion throughput naturally impacts sensitivity. Despite this limitation, a suite of vendors have begun producing a range of mobility-based instruments, including DT-IMS systems, for the research community, and this access has further propelled adoption of the technique.

While these ion mobility-mass spectrometry (IMMS) instruments enable for a broad class of researcher, they are still limited by duty cycle and sensitivity, which constrains their ultimate potential. These classic trade-offs are by no means new problems, but few solutions have been wholly adopted by the community.

Particular solutions applied to combat the duty cycle problem include multiplexing approaches such as Fourier and Hadamard pulsing schemes, which independently enhance the throughput of ion mobility spectrometry (IMS) experiments. Historically however, FT-IMS experiments, for example, never realized the full Signal to Noise Ratio (SNR) potential suggested by theory. As a result, challenges nonetheless remain as to the broad scale implementation using such techniques when utilized with ion mobility mass spectrometry (IMMS) instruments.

Accordingly, a need exists for a hybrid Perturbation Ion Mobility Mass Spectrometry (PIMMS) system and methodology that increases the system's duty cycle and sensitivity while maintaining equivalent resolving power. In the embodiments herein, ions are continuously introduced into a drift tube cell of a configured ion mobility spectrometer and then periodically, the continuous ion beam is perturbed and the perturbation continues to travel through the tube with the mobility matching the ions in the ion beam. By monitoring the disappearance of an ion in the mass spectrometer, the ion mobility spectrum is reconstructed and the size of an ion (its mobility) is measured as a function of its mass. In addition to an improvement in duty cycle, perturbation IMMS can additionally be used with MSMS techniques and is particularly useful for coupling to chromatographic separation instrumentation and methodologies.

SUMMARY OF THE INVENTION

A particular aspect of the embodiments herein is directed to a perturbation ion mobility spectrometer method for analyzing ion populations, that includes: directing a continuous gas phase ion beam comprised of a plurality of ions into an entrance of a drift tube configured within an ion mobility spectrometer; perturbing the flow of the continuous gas phase ion beam within a perturbation time range so as to cause one or more configured perturbations of the continuous gas phase ion beam; configuring the drift tube to allow the one or more perturbations to separate due to the differences in mobilities of the plurality of ions; receiving the plurality of ions and the one or more perturbations at the entrance of a mass spectrometer; recording raw data indicative of the plurality of ions that are received by the mass spectrometer that comprises: a mass to charge ratio of the plurality of ions, an intensity change of the plurality of ions caused by the one or more perturbations, and the arrival times of the one or more perturbations; and reconstructing the raw data to obtain one or more mass to charge and one or more ion mobility spectrum of the plurality of ions.

Another of the embodiments herein is directed to a perturbation ion mobility mass spectrometer apparatus for analyzing ion populations, including: a drift tube configured as part of an ion mobility spectrometer, wherein the drift tube is further configured to receive a continuous gas phase ion beam comprised of a plurality of ions; an ion gate configured to cause one or more perturbations of the flow of the continuous gas phase ion beam within the drift tube, wherein the drift tube is further configured to allow the one or more perturbations to separate due to the differences in mobilities of the plurality of ions; a mass spectrometer configured to receive at least a portion of the plurality of ions and the one or more perturbations; and one or more sensors and one or more electronics for recording raw data indicative of the plurality of ions that are received by the mass spectrometer that comprises: a mass to charge ratio of the plurality of ions, an intensity change of the plurality of ions caused by the one or more perturbations, and the arrival times of the one or more perturbations.

Accordingly, the methodologies herein provide for a system and methodology wherein ions introduced as a pulse into the drift region of the ion mobility spectrometer and the ion beam's perturbation separate by mobility. This perturbation in the ion beam may be a gap, waveform, or even an increase in signal intensity. By monitoring the disappearance of an ion in the mass spectrometer, the ion mobility spectrum is reconstructed and the size of an ion (its mobility) can be measured as a function of its mass. This Perturbation IMMS approach increases the duty cycle from a typical 1% for the standard pulsed technique to more than 99%. To illustrate, in a conventional IMMS instrument methodology using 75 milliseconds (ms) as a spectrum length and with a configured 0.1 ms ion-gate pulse-width, the ion efficiency is 0.1/75=0.133%. By contrast, using Perturbation IMMS, as disclosed herein, with 75 ms per spectrum and with a 0.1 ms of perturbation (time stoppage of the flow of ions), ion efficiency 74.9/75=99.867%. Accordingly, as a surprising result, the embodiments herein provide for an improvement of ion efficiency is 74.9/0.1=749 times, a number that also allows for an improvement in signal-to-noise ratio.

In addition, because of the resultant improvement in duty cycle over IMMS, PIMMS is capable of being used with MSMS techniques and with a stand-alone IMS instrument. Moreover, PIMMS is particularly useful for coupling IMMS with chromatographic separation methodologies and systems.

BRIEF DESCRIPTION OF THE DRAWINGS

FIG. 3A shows isotope ratios of various tetra alkyl ammonium (TXA) ions under the perturbation mode of operation, as disclosed herein.

FIG. 3B shows isotope ratios of various TXA ions with various gate pulse widths under the normal pulsed mode so as to compare with the data shown in FIG. 3A.

FIG. 5A shows tetraalkylammonium spectra (T5A) to illustrate the capability of providing resolving power using the perturbation mode in comparison of the resolving power in a normal pulsed mode of operation.

FIG. 5B shows tetraalkylammonium spectra (T7A) to illustrate the capability of providing resolving power using the perturbation mode in comparison of the resolving power in a normal pulsed mode of operation.

FIG. 5C shows tetraalkylammonium spectra (T10A) to illustrate the capability of providing resolving power using the perturbation mode in comparison of the resolving power in a normal pulsed mode of operation.

FIG. 5D shows tetraalkylammonium spectra (T12A) to illustrate the capability of providing resolving power using the perturbation mode in comparison of the resolving power in a normal pulsed mode of operation.

FIG. 6A shows transmission intensity efficiencies of the mass only mode (i.e., open mode) to provide a comparison of mass spectral intensities of tetra alkyl ammoniums between the mass-only, normal pulsed mode, and perturbation modes of operation.

FIG. 6B shows transmission intensity efficiencies in the gating period of the normal pulsed mode to provide a comparison of mass spectral intensities of tetra alkyl ammoniums between the mass-only, normal pulsed mode, and perturbation modes of operation.

FIG. 6C shows transmission intensity efficiencies in the perturbation mode (i.e., open mode) to provide a comparison of mass spectral intensities of tetra alkyl ammoniums between the mass-only, normal pulsed mode, and perturbation modes of operation.

DETAILED DESCRIPTION

Figure 1:
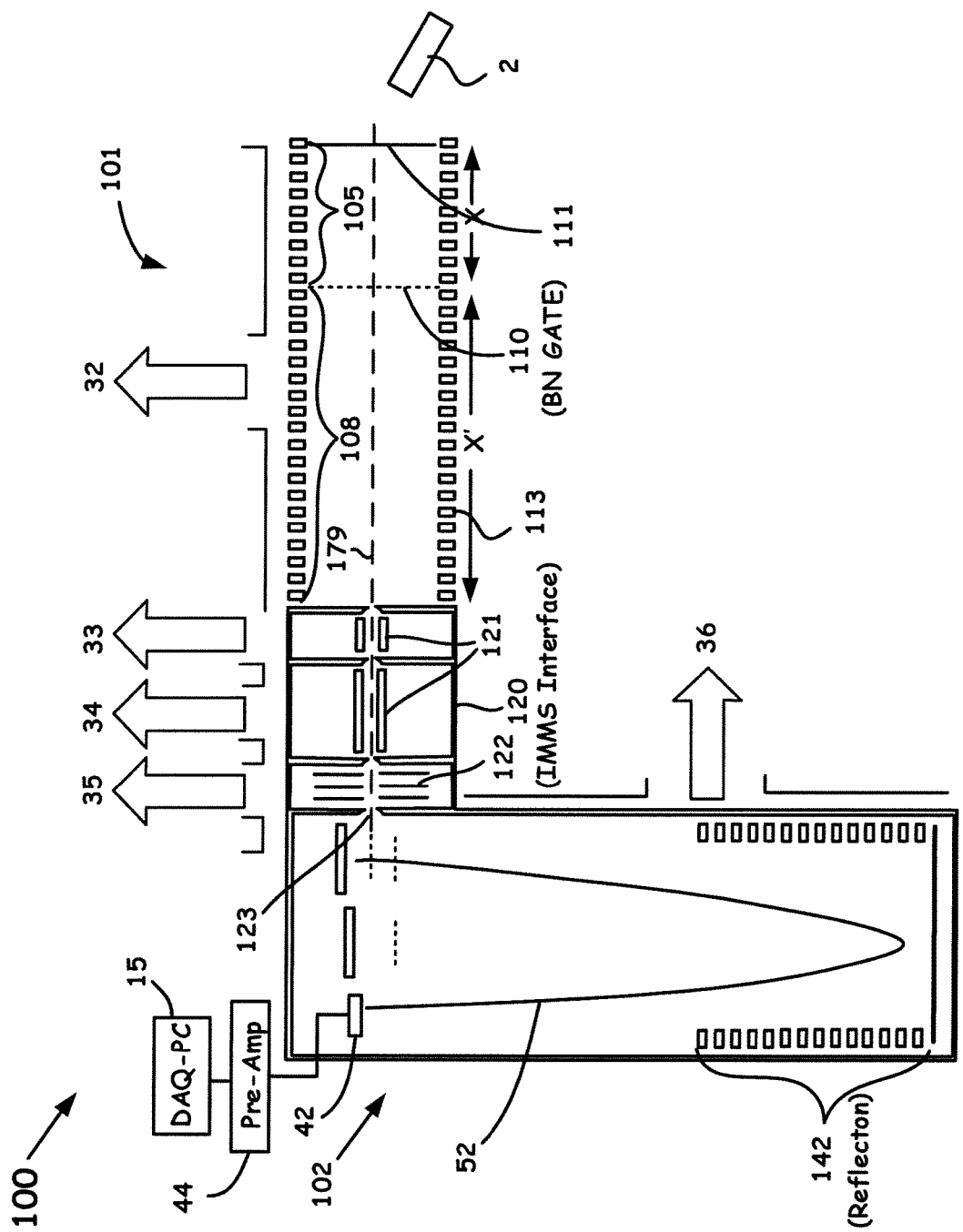
FIG. 1 illustrates an example embodiment of a single gate Ion Mobility drift tube interfaced to a Compact Time of Flight Mass Spectrometer.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

GENERAL DESCRIPTION

Drift tube ion mobility spectrometry (DT-IMS) can be operated under different pressure conditions, from ambient to vacuum; in this invention. The example embodiments herein are directed to a novel methodology and hybrid system apart from conventional ion mobility mass spectrometry. In particular, the system(s) and methodologies herein, introduces ions continuously into a drift tube cell (ambient or vacuum pressure configurations) of a configured ion mobility spectrometer and then periodically, the continuous ion beam is perturbed by chopping the flow of ions for a very short period of time, as disclosed herein. Often the deflecting, modulating, interrupting, chopping or perturbing of the flow of the continuous ion beam, (i.e., perturbing or the perturbation) is by use of an electro-driven device, as shown herein, as controlled by a pulse generator to create the short periods of perturbation time. The perturbation continues to travel through the tube according to the matching mobility (or drift time) of the ions in the ion beam.

When several ions are present in the IMS cell, these perturbations separate due to the differences in mobilities of the ions in the cell. The perturbation can result in only a 0.05% up to about a 1% loss in ions, leaving more than 99% of the total ions for detection from the continuous ionization source, which is a great improvement over conventional technologies. The ion beam, with its mobility separated perturbations, is then guided into the mass spectrometer. The ions are recorded based on their mass to charge ratio in a mass spectrometer and the intensity change, caused by the perturbation, along with the arrival time of the ion perturbation time, are recorded. The ion mobility spectra are then reconstructed based on the intensity change, perturbation interval, and perturbation period. Such a methodology applied to a number of types of ion mobility mass spectrometers beneficially leads to an improvement in sensitivity from at least 100 times up to 14000 times without loss of the resolving power of the ion mobility spectrometer.

Accordingly, a basis of the present invention is directed to providing ion detection efficiency and thus enhanced sensitivity for mobility measurements using hybrid instruments disclosed herein. Moreover, the embodiments herein are additionally capable of being coupled to beneficial chromatographic methods, such as, but not limited to: ultra-performance liquid chromatography, high performance liquid chromatography, gas chromatography, supercritical fluid chromatography, capillary electrophoresis, etc., without sacrificing sensitivity. The efficiency and accuracy of qualitative analysis are also improved.

SPECIFIC DESCRIPTION

FIG. 1 illustrates an example embodiment of a Perturbation Ion Mobility Mass Spectrometry (PIMMS) system, as generally designated by the reference numeral 100, which includes an ion mobility spectrometer 101 coupled to a mass spectrometer 102, configured to operate according to aspects of the configurations disclosed herein. While the system 100 of FIG. 1 is beneficial for illustrative purposes, it is to be understood that other alternative commercial and custom ion mobility and mass spectrometer configurations and various components, as known in the art, can also be incorporated when using the perturbation ion mobility mass spectrometry (PIMMS) approach disclosed herein.

Nonetheless, components of note, as shown in FIG. 1, include an ion source 2, the aforementioned ion mobility spectrometer 101 and the mass spectrometer, which as an exemplary instrument for the disclosure herein, is a time-of-flight (TOF) spectrometer 102. It is to be appreciated that while a TOF 102 is shown in FIG. 1, of which can include a reflectron 142, other types of mass spectrometers (e.g., a quadrupole mass analyzer, a two-dimensional ion trap, a three dimensional ion trap, a time-of-flight (TOF), an oribitrap, and a FT-ICR device, etc.

The ion mobility spectrometer (IMS) 101 shown in FIG. 1, is also often comprised of, a heated desolvation region 105 as known in the art, having a length X, a drift region 108 having a length X', a perturbation means 110 (e.g., a Bradbury-Nielsen ion gate) coupled to an Ion Mobility Mass Spectrometer Interface (IMMS) 120.

In operation, a sample containing one or more analytes of interest can initially be ionized via ion source 2 using any of the applicable techniques known and understood by those of ordinary skill in the art. While FIG. 1 depicts an Electrospray Ionization (ESI) configuration as the example ion source 2, a variety of other configurations to provide ions of interest can also be incorporated. Example sources include, but are not limited to, Atmospheric Pressure Ionization (API), Atmospheric Pressure Chemical Ionization (APCI), Nanoelectrospray Ionization (NanoESI), thermospray ionization, electron impact (EI) ionization, chemical ionization (CI) source, an EI/CI combination ionization source, a corona discharge source, or any other source that can be utilized without departing from the scope of the invention.

Turning back to FIG. 1, a resultant flow of ions is urged through a series of chambers of often, but not necessarily, progressively reduced pressure with a number of ion optics utilized, as known in the art that operationally guide such ions to provide desired transmission efficiencies. As generally shown in FIG. 1, the various chambers often communicate with corresponding ports 32, 33, 34, 35, and 36 (represented as arrows in the figure) that are coupled to a set of pumps (not shown) to maintain the pressures at the desired values. Non-limiting example pressures for illustrative purposes only are about 712 Torr or greater for chamber(s) coupled to port 32, 1.5-3 Torr for chamber coupled to port 33, $10^{-3}$ Torr for chamber coupled to port 34, $10^{-6}$ Torr for chamber coupled to port 35, and $10^{-7}$ Torr for chamber coupled to port 36. A non-limiting example desolvation length X is at about 10 cm and an example length for the drift region X' is at about 21.5 cm for the IMS portion 101 shown in FIG. 1. While such pressures are disclosed above, it is also to be noted that the drift tube region 108 and corresponding port 32 can also be configured to operate at ambient or in vacuum pressure situations when desired, of which also comports with the scope and spirit of the present embodiments herein.

In general, an interfering disturbance via the perturbation means 110 is applied to a stream of ions generated by the ion source 2. The perturbation means 110 utilized herein, as a beneficial non-limiting example, is comprised of a configured grid of closely arranged wires alternately supplied with different potentials. In operation, the stream of ions are attracted to the wires having configured potentials and thus are discharged to block the flow of ions to provide a perturbation to the ion flow. If the system 100 as per the controller/PC 15 as shown in FIG. 1, removes the potentials, the gate 110 is switched to be an open state wherein the ions enter the remaining part of the drift region 108 as a continuous ion stream and are pulled through the drift region by the electric field as provided by the ring electrodes 113 (one denoted for simplicity).

The perturbation means 110 described above is by convention, a configured Bradbury-Nielsen gate. However, it is to be noted that such a configuration can also be substituted with other suitable means to disturb (perturb) the flow of ions within the drift region 108 of the IMS 101. For example, such other suitable means include mechanically controlled devices such as a rotor-driven ion shutter or an alternative electro-driven device, such as a reverse electric field (Tyndall gate) to the drift field. Moreover, the disturbance device also can also be a configured ion trap, an ion pusher, or other device that stores or expel ions in a short period-of-time or even configuring an ESI source to be modulated in conformity with the embodiments disclosed herein.

As noted above, a controller/PC 15 provides the signals for the gate 110 perturbation and is used to interpret (i.e., using signal processing) the information enabled by the coupled time-of-flight (TOF) instrument 102. With respect to the TOF 102, as shown in FIG. 1, as ions enter the TOF and directed along a path 52, ion current is received via the detector 42 (e.g., a multi-channel plate) and amplified (i.e., via pre-amp 44). Thereafter, via controller/PC 15, the amplified ion current signal is stored as digitized information (e.g., using a digital converter) and signal processed using custom but more often commercial software (e.g., Igor) and transformation methods disclosed herein, e.g., using Fourier and/or Hadamard transforms or other methodologies (e.g., Barker code) known and understood by those of ordinary skill in the art.

The controller/PC and data acquisition system itself (generally referenced by the numeral 15) is to be noted of various circuitry of a known type. Such a control and data system can be implemented as any one of or a combination of general or special-purpose processors (digital signal processor (DSP)), firmware, software, graphical user interfaces (e.g., LabVIEW) and/or hardware circuitry to provide instrument control, RF and DC power, and data analysis, etc., for the example configurations disclosed herein.

It is also to be appreciated that instructions to operate the system shown in FIG. 1, which include the enabling of desired RF and DC voltages, the control of pressure via pumping means known in the art, the identifying of m/z values, drift times, cross-sectional areas of the ions, the merging of data, the exporting/displaying/outputting to a user of results, etc., may be executed via for example the controller/PC 15, which includes hardware and software logic for providing the instructions and control functions of the system 100.

In addition, such instructions and control functions, as described above, can also be implemented by the system 100, as shown in FIG. 1, configured to operate via a machine-readable medium (e.g., a computer readable medium). A computer-readable medium, in accordance with aspects of the present invention, refers to media known and understood by those of ordinary skill in the art, which have encoded information provided in a form that can be read (i.e., scanned/sensed) by a machine/computer and interpreted by the machine's/computer's hardware and/or software.

In the general operation of the system 100 shown in FIG. 1, the ion source 2, often an electrospray ionization source (ESI), configured at about 45 degrees provides desired ions. Such ions are gated (allowed to pass) using any number of known in the art gates (e.g., gate 111) into the desolvation region 105 to substantially remove water clusters and desolvate gaseous analytes so as to aid in improving signal-to-noise within a given MS spectrum. The desolvation of ions may be aided by a constant counter current flow between 0.1-10 L/min of gas held at 50-500° C. Any gas (or mixtures thereof) suitable for use in an IMS instrument may be utilized in practice of aspects of the invention, such as, but not limited to Nitrogen, Carbon Dioxide, Oxygen, Nitrous Oxide, Noble Gasses, Sulfur hexafluoride, and combinations thereof.

As shown generally in FIG. 1, the drift region 108 as well as the desolvation region 105 includes electrodes 113 configured as differing sets of conducting drift rings. Ions enter the drift region 108 using the aforementioned perturbation means 110, as directed by the system 100, using the methods disclosed herein. Such admitted ions can then move (drift) with individual characteristic velocities within the drift region 108 under a constructed electric field provided by the electrodes 113.

After exiting the drift region 108, ions are directed to a reduced pressure region interface (i.e., the chamber coupled to port 33) referred to overall as the Ion Mobility Mass Spectrometer Interface (IMMS interface 120). As generally shown in FIG. 1, the IMMS interface 120 includes electrode guides (e.g., quadrupoles 121 and ion optics 122) for urging the ions of which eventually are directed through a pinhole (generally referenced by numeral 123) before being received by the TOF 102 shown in FIG. 1. It is to be noted that the configuration of system 100 shown in FIG. 1 shows an axis 179 for the IMS 101 perpendicular to the TOF 102 instrument and thus perpendicular to the flight ion flight path 52. While such a configuration is beneficial in some aspects, e.g., ion packets entering the ion acceleration region of the TOF 102 are more likely to have constant and more defined initial ion positions, it is also to be noted that non-perpendicular configurations can also be utilized without departing from the scope of the invention.

Thereafter, as known to those of ordinary skill in the art, TOF 102 operates to separate ions in time according to their individual masses. Generally, ions having less mass will reach the detector 42 faster than those having greater mass. The detector 42 is configured to receive arrival times of the ions, perturbation intervals, and perturbation times to provide signals corresponding to such ions, perturbation intervals, and perturbation times, wherein the controller/PC thereafter can then operate on the received signals using signal processing methodologies, as disclosed herein.

To reiterate, as briefly discussed above, by periodically imposing a perturbation to the stream of ions in the IMS 101 device using the perturbation means 110, a gap in the ion beam is produced. Thus, instead of entering as a pulse into the drift region 108 of the ion mobility spectrometer 101 and separated by their mobilities, using the teachings herein, the location of the minimum ion current signal denotes an ion packet's mobility. By periodically disturbing the incoming ion stream in such a manner, the perturbed ion current can be monitored to associate reductions in ion current on a m/z basis with mobility of the target analyte. Specifically, the additional dimension of m/z allows for the mobility to be reconstructed and the signal further enhanced by applying m/z-specific signal processing approaches. Such an overall construction and overall methodology has never been accomplished in practicality.

To aid the reader in understanding the possible various embodiments of the present invention, the following provides reference when considering designing the Perturbation Ion Mobility Mass Spectrometer instrument in combination with signal reconstruction methodologies herein, which is intended to be illustrative only, but not limiting thereof.

EXAMPLE

Perturbation Ion Mobility Mass Spectrometer

Signal processing experiments were conducted using an example ion mobility system 100, as shown in FIG. 1, capable of being interfaced to a compact time of flight mass spectrometer (TOF-MS, TOFWERK, Thun, Switzerland). This instrument/system 100, based upon a stacked-ring drift tube design, as briefly discussed above, is capable of operation from ~100 to 250° C. with a homogeneous electric field of ~350 V/cm. Counter-current flow of high-purity, dry nitrogen can be introduced at the exit of the drift cell at ~1 L/min and atmospheric pressure. Following ionization using an electrospray ionization source (ESI) 2, ions traversed a short desolvation region before encountering the perturbation means (BN-gate) 110. The interface between the IMS 101 and the TOF region of the MS 102 comprised of a pinhole nozzle with a 300 μm diameter. The pressure inside the interface can be, when warranted, stepped down in two stages, from atmospheric pressure (approximately 950 mbar) to 2-4 mbar within the interface. The mass spectrometer 102 operated with a V mode to achieve higher sensitivity and higher sampling rate to keep up with the speed of ion mobility separation.

The perturbation means (e.g., a BN-gate) 110 frame was constructed using two 99% alumina rings (50 mm ID×58 mm OD×3.5 mm thick) that served to hold two electrically isolated sets of parallel wires made of Alloy-46 (California Fine Wire Co., Grover Beach, Calif.). The wire was approximately 75 μm in diameter and the spacing of the BN-gate 110 was 0.64 mm. The entire gate assembly was held together using a high temperature ceramic epoxy supplied from Cotronics (Resbond 940, Brooklyn, N.Y.).

The choice of materials for the perturbation means (BN-gate) 110 enabled matching the thermal coefficients of expansion to maintain gate integrity. Perturbation of the BN-gate (+/−46 V) is accomplished using a custom floating power supply which enabled ions to enter the drift tube (e.g., a 23 cm-long drift tube) coupled to the TOF-MS 102. The gate pulse utilized varied in the perturbation mode often with a gating close time, i.e., the perturbation, from about 144 μs to up to about 1200 μs as applied to the adjacent gating wires. However, it is to be appreciated that while such a perturbation closing time was utilized, the perturbation time for perturbing the ion flow has been shown to be beneficial within a perturbation time range from about 5 μs up to 10 ms at a constant interval of 25 ms to 250 ms.

The electric field across the IMS drift region was 313 V/cm. The temperature of the IMS was operated at either 75 or 120° C. depending on the class of experiment conducted. While pressure was 93.3 kPa during the experiment, this can vary based on other configured parameters. A 6 cm long 75 μm ID and 150 um OD silica capillary tube with polyimide coating was used as an electrospray emitter (ion source 2) and installed 8 mm behind a shielding screen. A 2.4 kV bias potential was often applied to the ESI needle relative to the drift voltage of the drift tube. The electrical potential used to produce ESI was applied through a stainless steel zero dead volume union (Valco Instruments, Houston, Tex., U.S.A.) that connected the emitter with the fused-silica capillary transfer line (360 μm o.d.×75 μm i.d., ~30 cm long.

Spectral data were acquired using a time-to-digital converter (HPTDC-PCI, Cronologic, Frankfurt, Germany), as part of the controller 15 and as enabled by commercial (e.g., TOFWERK) software which produced output files. Once imported into Igor Pro (an interactive software environment for experimentation with scientific and engineering data), the m/z-specific drift times can be and were extracted. Perturbation mode IMMS spectra are thereafter obtained by inverting the baseline of ion intensity spectra followed often by a denoising procedure leveraging a transform (e.g., a Fourier Transform) and removal of high frequency noise.

As a beneficial aspect of the embodiments herein, the resolving powers of each ion peak are capable of being calculated when desired. Such a calculation entails taking the resultant drift time ($t_d$) (as recorded by the embodiments herein) of the ion divided by the full peak width at half height ($w_{0.5}$) of the ion mobility peak as shown by Equation 1 as follows:

$$R_m = \frac{t_d}{w_{0.5}} \tag{1}$$

where $R_m$ is a measured resolving power.

Chemicals and Reagents

A range of tetraalkylammonium salts (Sigma-Aldrich, St. Louis, Mo.) were used to evaluate the performance of the FT-IMMS technique relative to the signal averaging experiments. More specifically, the following salts were used: tetrapropylammonium bromide (T3A), tetrabutylammonium bromide (T4A), tetrapentylammonium bromide (T5A), tetrahexylammonium bromide (T6A), tetraheptylammonium bromide (T7A), tetraoctylammonium bromide (T8A), tetradecylammonium bromide (T10A), tetradodecylammonium chloride (T12A). A 100 μM stock solution was prepared in 50% acetonitrile and 0.1% formic acid and further dilutions were made to realize final concentrations used during the evaluations.

Signal Processing, and Data Transformation/Results

Generally, in a normal, signal averaged pulsed mode, as understood by those of ordinary skill in the art, a duty cycle of less than 1% (200 μs pulse width divided by 60 ms scan time) is more often resultant from an ion mobility spectrometer system. Those skilled in the art also understand that this in reality means that more than 99% of ions are lost to the gating wires during the closed gating stage.

Thus, when operating in a "normal, signal averaged pulsed mode," conventionally, those skilled in the art note consequences when coupling an ion mobility system to a mass spectrometer. First, when using volatile analytes, neutral molecules are routinely swept out of the system using a countercurrent flow of gas; however, when lower volatility compounds are used, the ion gate wires may become contaminated as neutralized analytes deposit. Additionally, the deposition of analytes onto the ion gate wires can alter the electric field in the gating region and directly influence transfer efficiency of the system. Second, sensitivity is more often significantly decreased due to the low duty cycle, which hinders efforts to couple chromatography to ambient and/or low pressure ion mobility mass spectrometry systems.

However, it is to be appreciated by the disclosure herein that by interfacing perturbation ion mobility to mass spectrometry, which in practice, has hereinbefore not been accomplished, the duty cycle is capable of being increased to more than 99%. Thus, in a novel and unobvious manner, substantially all of the ions pass the ion gate and are detectable by a system, such as that as shown in FIG. 1 and beneficially lead to an improvement in sensitivity of 100 to 1000 times.

Moreover, because the present embodiments are very easy to operate in different ion mobility mass spectrometers, the disclosed system(s) herein are also beneficial for coupling to chromatographic methods, such as, for example, ultra-high-performance liquid chromatography, high-performance-liquid chromatography, gas chromatography, supercritical fluid chromatography, capillary electrophoresis and other separation techniques without a sacrifice in sensitivity. The efficiency and accuracy of qualitative analysis are also improved greatly.

Figures 2A, 2B, 2C:
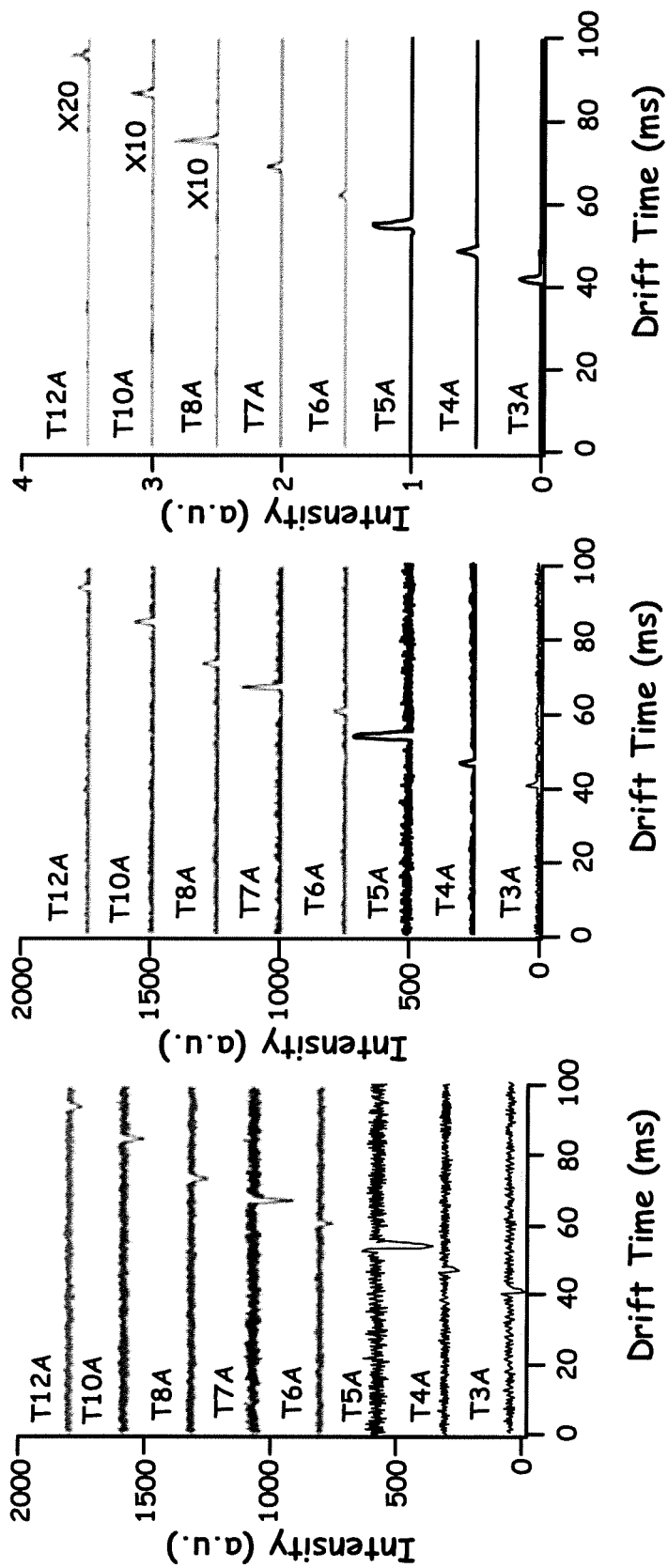
FIG. 2A shows a Perturbation IMMS mode spectra plot of intensity versus drift time in milliseconds of the present embodiments with the use of a gate pulse width of 1080 µs.
FIG. 2B shows a reconstructed Perturbation IMMS mode plot of intensity versus drift time in milliseconds.
FIG. 2C shows a normal, signal averaged pulsed mode plot of intensity versus drift time in milliseconds when operating with a gate pulse width of 600 µs.

Turning to the figures, FIG. 2A, FIG. 2B, and FIG. 2C show typical m/z-specific mobility traces extracted from the two-dimensional ion mobility mass spectrometry spectrum for eight tetraalkylammonium (TXA) ions. In particular, FIG. 2A shows a perturbation IMMS mode spectra plot of intensity versus drift time in milliseconds of the present embodiments with the use of a gate pulse width of 1080 μs. FIG. 2B shows a reconstructed perturbation IMMS mode plot of intensity versus drift time in milliseconds and FIG. 2C shows a normal, signal averaged pulsed mode plot of intensity versus drift time in milliseconds when operating with a gate pulse width of 600 μs. While TXA ions are not representative of all ions, they do provide an ion set covering a wide range of mobilities to illustrate the workings of the present embodiments.

It is to be noted that FIG. 2C shows that when operating in a normal, signal averaged pulsed mode, T3A, T4A, and T5A were the three dominant peaks with the other TXA ions exhibiting much lower intensities. For T10A and T12A, only trace level signals were obtained using the same acquisition time. Overall, FIGS. 2A-2C demonstrate the effects of the duty cycle differences between the normal, signal averaged pulsed mode, as shown in FIG. 2C, and the perturbation mode disclosed herein, shown in FIG. 2A, have on the observed peak profiles. Specifically, in the perturbation mode, as shown in FIG. 2A, ions were steadily detected in the mass spectrometer throughout the whole drift period except for the ion gaps created by briefly perturbing the ion flow by placing the ion gate briefly in the closed mode.

Though all analyte ions showed ion gaps at their characteristic mobilities, raw two-dimensional spectrum of the perturbation mode was very different from that of the normal pulse mode (data not shown). However, a close examination of the m/z extracted mobility data could be reconstructed in a fashion to produce spectra that were similar to the normal pulse mode operation.

These data, shown in FIG. 2B, were reconstructed by subtracting the intensity of the averaged response of each ion from their raw data. A detailed accounting of the reconstruction approach is addressed below. It is worth noting that, in normal pulsed mode, the intensity profiles of 3 TXA ions, T8A, T10A, and T12A, were scaled by X10, X10, and X20, respectively, for visual clarity. A cursory comparison between FIG. 2B and FIG. 2C suggests that the signal-to-noise ratios (SNR) between the normal pulsed mode (FIG. 2C) and the perturbation modes (e.g., FIG. 2B) of operation differ.

However, the trade-off between SNR in the mobility domain must be balanced with the signal fidelity found in the resulting m/z spectra. In the normal pulse mode of operation, the mobility peaks emerge from the baseline as a positive signal, whereas, in the perturbation mode, negative perturbations in the signal produced from the ion source correspond to mobility. Nevertheless, a benefit of perturbation ion mobility mass spectrometry is the production of mass spectra that more closely resembled theoretical profiles of target ion species. Isotopic profiles and relative abundances of common target ions is an important analytical metric to many applications, such as quantitative isotopic labeling experiments, radiological dating, and molecular identification.

FIG. 3A and FIG. 3B compare the isotope ratios of various TXA ions with various gate pulse widths under the normal pulsed mode and perturbation mode of operation. In particular, FIG. 3A and FIG. 3B show isotope ratio comparisons between normal pulsed mode (e.g., FIG. 3B) using various gate pulse widths (e.g., GPW 120=a Gate pulse width of 120 μsec) and the perturbation mode (e.g., FIG. 3A) of the present embodiments. Theoretical isotope profiles were generated using IMSviewer2.0e with a full width half maximum (fwhm) of 150 ppm for each TXA ion. The theoretical isotope profiles included the monoisotopic peak and the three major isotope peaks, and the theoretical mass peaks were compared using a correlation. FIG. 3A thus represents the comparisons for the perturbation mode whereas the lower bar graph set (e.g., FIG. 3B) was derived from normal mode data.

Because there were more ions available for statistical calculations in the perturbation mode, the isotope ratios between [M+1]+, [M+2]+, and [M+3]+ were closer to those determined by theoretic methods. However, the results of normal pulsed mode operation heavily depended on the gate pulse width. For short pulses, such as 120 μs, all eight ions investigated showed an undesired 20-92% bias from the theoretic results. Though prolonged gate pulse width improved this performance, the resolving powers are subsequently decreased.

Signal to Noise Ratio and Resolving Power of Perturbation Ion Mobility Mass Spectrometry To investigate the signal-to-noise ratio, individual mass selected ion mobility spectra were compared between the normal mode and the perturbation mode. Because of fluctuation of the electrospray ionization source, the baselines for the perturbation mode spectra were noisier than those of the normal pulsed mode with most of the baseline noise being dominated by high frequency signals. Thus, a low-pass filtering approach leveraging the fast Fourier transform (FFT) is adopted to reconstruct the spectra for the perturbation mode.

Figure 4:
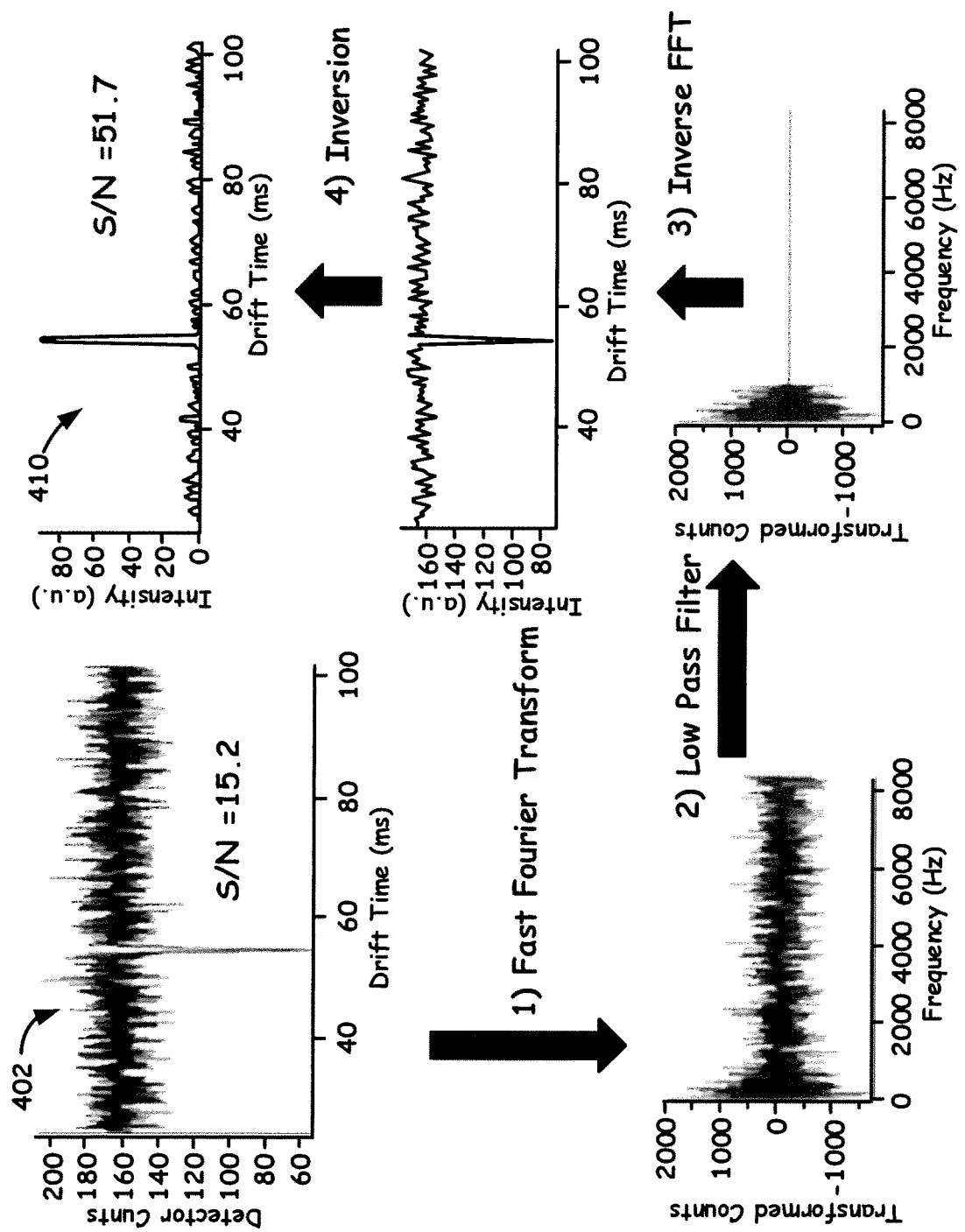
FIG. 4 shows a data processing workflow for perturbation ion mobility mass spectra that include: a Fast Fourier Transform of the raw data 402, a Low pass filter applied to the frequency domain, an inverse FFT to obtain a denoised spectrum, and inverting the spectrum to obtain a regular ion mobility spectrum.
Figure 5E:
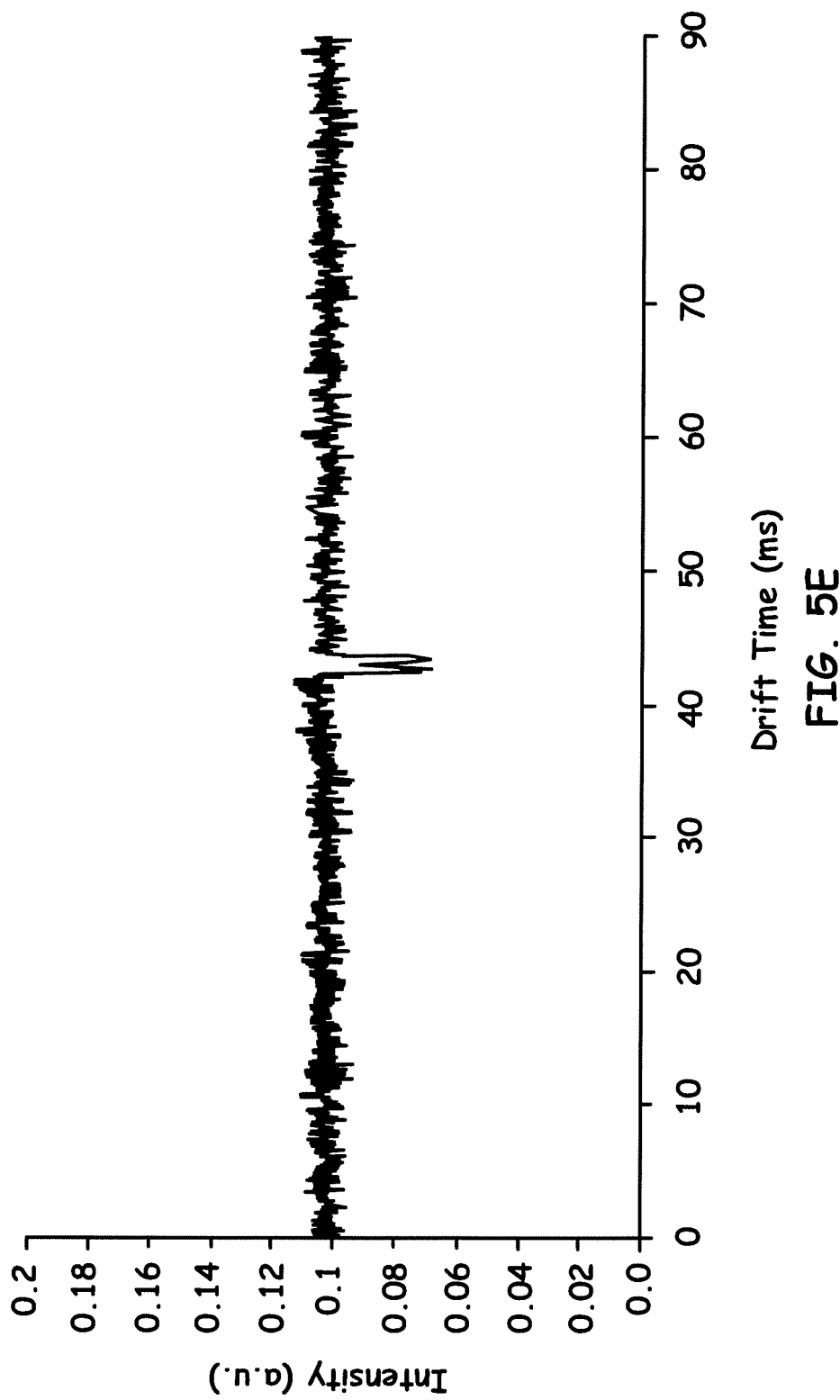
FIG. 5E shows a plot of intensity versus drift time in milliseconds of the resolution of Ractopamine diastereoisomers using PIMMS to illustrate the resolution capabilities (i.e., resolving power) of the present embodiments.

Accordingly, FIG. 4 demonstrates the steps comprising the mode of operation. In particular, FIG. 4 shows a data processing workflow for perturbation ion mobility mass spectra. Such steps include: Step (1) a Fast Fourier Transform of the raw data 402; Step (2) a Low pass filter applied to the frequency domain; Step (3) Inverse FFT to obtain the denoised spectra; and Step (4) Inverting the spectra to obtain a regular ion mobility spectrum 410.

Briefly, a Fourier transform frequency spectrum analysis was performed to obtain the signal and noise frequency distribution, as shown as Step 1) in FIG. 4. Next the high frequency components were discarded by driving the higher frequency components to zero. In our experimental conditions, any frequency higher than 150 Hz could be discarded without distorting peak shapes or peak positions following an inverse Fourier transform. Following the inverse transform, the data were inverted to produce a data representation that is more commonly used for viewing ion mobility data. It is important to note that the procedure herein improved the signal-to-noise ratio of T7A from 15.2 to 51.7. However, while such signals were beneficial in illustrating an improved signal-to-noise ratio, it is to be noted that the embodiments herein have been shown to overall improve the signal-to-noise signal-to noise ratio from 1.1 up to 1,000,000 times when using reconstructing signal processing techniques, as disclosed herein. The techniques herein are also directed to improving the resolving power. However, in implementing the procedure herein, the ion current was about 0.5 nA, which results in a lower charge density. Accordingly, a configured higher ion current would provide a higher charge density and would more than likely improve the resolving power to higher desired levels.

FIG. 5A, FIG. 5B, FIG. 5C, and FIG. 5D show similarities of resolving powers for the conventional normal pulsed mode of operation and the disclosed perturbation mode of operation. Specifically, FIG. 5A, FIG. 5B, FIG. 5C, and FIG. 5D show four tetra alkyl ammonium spectra, including T5A (see FIG. 5A), T7A (see FIG. 5B), T10A (see FIG. 5C), and T12A (see FIG. 5D). The resolving power of T10A (see FIG. 5C) under a normal pulsed mode was 94, while the correlated perturbation mode showed a resolving power of 92. Under the same conditions, the Perturbation IMMS mode and normal pulse mode showed almost the same resolving power. This similar resolving power under normal mode and Perturbation IMMS mode was also observed with T12A (see FIG. 5D), with a resolving power of 98 and 96 for normal mode and the disclosed herein PIMMS mode, respectively. For T5A (see FIG. 5A) and T7A (see FIG. 5B), the resolving powers under normal mode were 87 and 91, while 85 and 93 for the PIMMS mode. Thus, while there is an indication of similar resolving powers, it is must be noted that the charge density differences of all peaks were not strong enough to change the resolving power. Nevertheless, the separation efficiency of PIMMS remained within 5% of the theoretically predicted maximum. To illustrate this, a beneficial example plot of intensity versus drift time in milliseconds of the resolution of Ractopamine diastereoisomers using PIMMS is shown in FIG. 5E.

Ion Discrimination Effect

The transmission efficiencies for different ions were impacted by ionization, ion gating, drift field, ion mobility mass spectrometry interface, and the ion optics. The traditionally Bradbury-Nielsen ion gate modulates an ion beam from the ion source by applying a perpendicular electric field to the drift field that can neutralize ions. As stated previously, when the ion gate is closed, ions are neutralized and destroyed on the gating wires, thus, a depletion ion zone is formed orthogonal to the plane of the grid wires in both directions.

Theoretically, different drift voltages require different optimum gating voltages, and different ions require their own optimum gating voltages as well. However, for complex samples, ions with varying mobilities are routinely separated in the drift tube, and only a single gating voltage is applied for practical reasons. In order to prevent ion gate leakage, the applied gate voltages must be strong enough to stop all ions simultaneously. Unfortunately, this single gating voltage applied to different ions will result in different transmission efficiency under the same conditions. To explore the impact of ion gating using the perturbation ion mode on transmission, ion intensities of different ions using different gate pulse width under normal pulsed mode and perturbation mode were compared to the open or mass only mode. Under the mass only mode, the ion gate was continually in the open configuration during the entire sampling period, thus, eliminating the influence of the ion gate on ion transmission efficiency.

FIG. 6A, FIG. 6B, and FIG. 6C show transmission efficiency differences in the gating period to provide a comparison of mass spectral intensities of tetralalkylammoniums between the mass-only, normal pulsed mode, and perturbation modes of operation. Both normal pulsed mode FIG. 6B and the perturbation mode FIG. 6C have a gate pulse of 600 µs for illustration purposes of the invention. Accordingly, low mass ions had higher transmission efficiencies, while heavier ions demonstrated lower ion transmission efficiencies under normal pulsed mode FIG. 6B. This discrimination effect resulted in serious ion loss for larger molecules which translates into lower limits of detection for these species. If we define the intensities of TXA ions under mass only mode as the references of transmission efficiency for various ions, then various TXA ion transmission efficiencies under perturbation mode and normal pulsed mode could be compared. For the 8 TXA, the following equation 2) was used for the calculation of ion discrimination effect based on the final ion intensities:

$$TE_i\ \% = \frac{I_{TiA}}{I_{TiA(M)}D_C} \times 100 \qquad 2)$$

where TEi % is the relative ion transmission efficiency for selected ion, ITiA is the intensity of selected ion under normal pulsed mode or perturbation mode, and ITiA(M) is the intensity of selected ion under mass only mode. To compare with the perturbation mode, the TE % of normal mode was multiplied by the time difference of the duty cycle.

Figure 7:
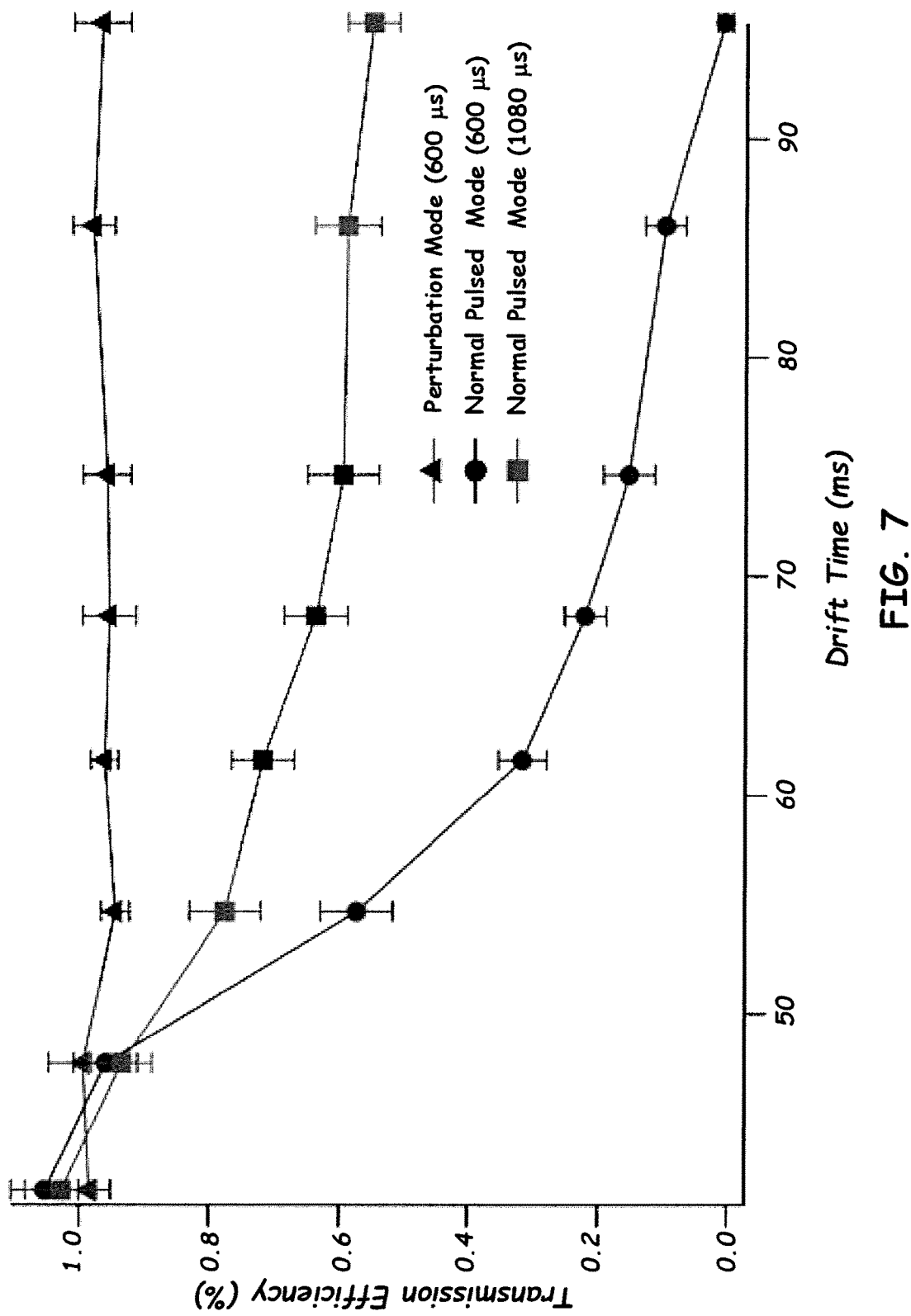
FIG. 7 shows the relative ion transmission efficiency for different tetra alkyl ammonium ions under normal pulsed mode of operation and the perturbation mode of operation so as to illustrate the impact of ion gate depletion.

The relative ion transmission efficiency is shown in FIG. 7. In particular, FIG. 7 shows the relative ion transmission efficiency for different tetra alkyl ammonium ions under normal pulsed mode (gate pulses of 600 µs and 800 µs) of operation and the perturbation mode (gate pulse of 600 µs) of operation so as to illustrate the impact of ion gate depletion. Each data point across the x-axis corresponds to 1 of the 8 tetraalkylammonium ions. In the normal mode, the ion transmission efficiency decreased rapidly as the drift time increases from T3A to T12A. For example, T4A produced a relative transmission efficiency of 97.2%, while T5A demonstrated a relative transmission efficiency of 54.64% compared to mass-only mode. For T6A, the TE % dropped to 31.71%. The heaviest ion investigated, T12A, showed a TE % of less than 1%. The change of relative transmission efficiency was mainly due to the gating efficiency of different ions, in which heavier ions traversed the gating wires slower than did the smaller ions. Because the axial drift velocity of the heavier ions is comparatively slow, these ions are subject to gate closing effects via "pull back", whereas the small, more mobile ions could pass the ion gate most efficiently. This mass discrimination effect led to lower sensitivities for heavier ions, especially when narrow gate pulse widths were used.

For perturbation ion mobility mass spectrometry, however, this discriminative effect was effectively eliminated by a significantly prolonged gate opening period, thus, various ions show similar relative transmission efficiency from T5A through T12A, varying from 95.2% to 98.9%. With this additional TE % gain, the ions' intensity differences between normal pulsed mode and the perturbation mode showed great differences for heavier ions. For example, the ion counts for T10A increased ~700 times, while the duty cycle increased ~180 times. One extreme example was the intensity differences between T12A under perturbation mode and normal pulsed mode, which increased ~14000 times. Longer gate pulse width for the normal mode largely alleviates this discriminative effect (e.g., 1080 μs); however, this operational mode significantly degrades resolving power. It is interesting to note that the smallest TXA ion selected, T3A, shows a higher TE % for normal mode over the perturbation mode. One reason for this phenomenon might be that the higher mobility of the light ions may have resulted in a high ion loss at the interface due to diffusion and Columbic repulsion. Thus, although few ions are allowed to pass the ion gate for the normal mode, the ion loss in the drift tube is less than perturbation mode for lower charge density.

Accordingly, as compared to conventional pulsed ion mobility mass spectrometry, PIMMS mode leverages a duty cycle that routinely exceeds 99%, while the traditional mode of operation often relies upon a <1% duty cycle. More importantly, the signal intensity for select ion classes is often improved by more than 2 orders of magnitude. In some cases, for low mobility ions, the gains in signal intensity can be more than 3 orders of magnitude, for these compounds are differentially affected by ion gating events using a Bradbury Nielsen ion gate.

It is to be noted that the resolving power of perturbation ion mobility mass spectrometry is similar to that of the normal mode, but the mass discrimination effect due to fast gating behavior is effectively eliminated in the perturbation ion mobility mass spectrometry experiment. The primary contribution to signal noise for the perturbation mode of operation is the stability of the ion source. Thus, for systems that rely on more stable ion sources (e.g., radioactive source), the perturbation mode of operation will be very beneficial. Most importantly, because such high duty cycles are achieved in the perturbation mode of operation, the approach herein enables the effective hyphenation of atmospheric pressure PIMMS systems with various chromatographic separation techniques, including gas chromatography, liquid chromatography, supercritical fluid chromatography, and electrophoresis instrumentation, while maintaining high resolving powers and improved levels of sensitivity compared to the traditional mode of operation.

In variety of the embodiments, a perturbation ion mobility mass spectrometer apparatus for analyzing ion populations is arranged so that an entrance of the drift tube configured within an ion mobility spectrometer allows for a continuous gas phase ion beam comprised of a plurality of ions to be received therein. Thereafter, an ion gate configured external to the entrance of the drift tube or downstream from the entrance perturbs (i.e., is perturbing) the flow of the continuous gas phase ion beam within a perturbation time range. By such an arrangement, configured perturbations of the continuous gas phase ion beam result and the drift tube, by its own electric field arrangement, as discussed above, allows the one or more perturbations to separate due to the differences in mobilities of the plurality of ions. An entrance of a mass spectrometer receives at least a portion of the plurality of ions and the one or more perturbations and sensors and electronics for recording raw data indicative of the plurality of ions to reconstruct the information using signal processing techniques. Raw data can include: a mass to charge ratio of the plurality of ions, an intensity change of the plurality of ions caused by the one or more perturbations, and the arrival times of the one or more perturbations. The ion gate is a common component used in the state of art DT-IMS systems; the ion gate is commonly used to allow or stop the ion beam at the entrance of the drift region of the drift tube by electrically opening and closing the gate. In this invention, the ion gate refers to a component that can in general be used to perturb the ion beam; the perturbation may be simply stopping the continuous ion beam, or the perturbation may include deflecting, modulating (even modulating an ESI ion Source), interrupting, chopping, etc. the ion beam.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A perturbation ion mobility mass spectrometer method for analyzing ion populations, comprising:
   directing a continuous gas phase ion beam comprised of a plurality of ions into an entrance of a drift tube configured within an ion mobility spectrometer;
   perturbing the flow of the continuous gas phase ion beam within a perturbation time range so as to cause one or more configured perturbations of the continuous gas phase ion beam;
   configuring the drift tube to allow the one or more perturbations to separate due to the differences in mobilities of the plurality of ions;
   receiving the plurality of ions and the one or more perturbations at the entrance of a mass spectrometer;
   recording raw data indicative of the plurality of ions that are received by the mass spectrometer that comprises: a mass to charge ratio of the plurality of ions, an intensity change of the plurality of ions caused by the one or more perturbations, and the arrival times of the one or more perturbations; and
   reconstructing the raw data to obtain one or more mass to charge and one or more ion mobility spectrum of the plurality of ions.

2. The method of claim 1, wherein the reconstructing step further comprises:
   subtracting the intensity of the averaged response of each ion of the plurality of ions from their raw data.

3. The method of claim 1, wherein the reconstructing step comprises:
   transforming of the raw data;
   low pass filtering a frequency domain of the transformed raw data;
   obtaining a denoised spectra of the frequency domain; and
   inverting the spectra to obtain a regular ion mobility spectrum.

4. The method of claim 3, wherein the reconstructing step enables an increase in signal-to-noise ratio, in a range of 1.1 to 1,000,000 times.

5. The method of claim 1, wherein the perturbing step includes a perturbation time range from about 5 µs up to 10 ms and at a constant interval of 25 ms up to 250 ms.

6. The method of claim 5, wherein the perturbation time range is from 144 µs up to about 1200 µs.

7. The method of claim 5, wherein the perturbation time provides for a duty cycle of at least 99%.

8. The method of claim 5, wherein the perturbation time range further enables an increase in sensitivity from 100 up to about 14000 times.

9. The method of claim 1, wherein the mass spectrometer is at least one mass analyzer selected from: a quadrupole mass analyzer, a two-dimensional ion trap, a three dimensional ion trap, a time-of-flight (TOF) analyzer, an orbitrap, and a FT-ICR analyzer.

10. The method of claim 1, wherein the drift tube is configured to operate in at least one of: an ambient condition and a vacuum pressure condition.

11. The method of claim 1, wherein the method includes coupling to at least one instrument selected from: an ultra-high-performance liquid chromatography instrument, a high performance liquid chromatography instrument, a gas chromatography instrument, a supercritical fluid chromatography instrument, and a capillary electrophoresis instrument.

12. A perturbation ion mobility mass spectrometer apparatus for analyzing ion populations, comprising:
a drift tube configured as part of an ion mobility spectrometer, wherein the drift tube is further configured to receive a continuous gas phase ion beam comprised of a plurality of ions;
an ion gate configured to cause one or more perturbations of the flow of the continuous gas phase ion beam within the drift tube, wherein the drift tube is further configured to allow the one or more perturbations to separate due to the differences in mobilities of the plurality of ions;
a mass spectrometer configured to receive at least a portion of the plurality of ions and the one or more perturbations; and
one or more sensors and one or more electronics for recording raw data indicative of the plurality of ions that are received by the mass spectrometer that comprises: a mass to charge ratio of the plurality of ions, an intensity change of the plurality of ions caused by the one or more perturbations, and the arrival times of the one or more perturbations.

13. The apparatus of claim 12, wherein the mass spectrometer is at least one mass analyzer selected from: a quadrupole mass analyzer, a two-dimensional ion trap, a three dimensional ion trap, a time-of-flight (TOF), an oribitrap, and a FT-ICR analyzer.

14. The apparatus of claim 12, wherein the drift tube is configured to operate in at least one of: an ambient condition and a vacuum pressure condition.

15. The apparatus of claim 12, wherein the apparatus includes at least one instrument selected from: an ultra-high-performance liquid chromatography instrument, a high performance liquid chromatography instrument, a gas chromatography instrument, a supercritical fluid chromatography instrument, and a capillary electrophoresis instrument.

16. The apparatus of claim 12, wherein the ion gate perturbs the flow of the continuous gas phase ion beam within a perturbation time range from about 5 µs up to 10 ms and at a constant interval of 25 ms up to 250 ms.

17. The apparatus of claim 16, wherein the perturbation time range is from 144 µs up to about 1200 µs.

18. The apparatus of claim 12, wherein the ion gate is selected from at least one of: a Bradbury-Nielsen ion gate, a Tyndall ion gate, an ion trap, an ion pusher, and a modulated electro-spray ion (ESI) source.

* * * * *